US009050421B2

(12) United States Patent
Bene

(10) Patent No.: US 9,050,421 B2
(45) Date of Patent: *Jun. 9, 2015

(54) FOLLOW-UP OF THE VASCULAR ACCESS OF A DIALYZED PATIENT

(71) Applicant: GAMBRO LUNDIA AB, Lund (SE)

(72) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 53 days.

This patent is subject to a terminal disclaimer.

(21) Appl. No.: 14/106,326

(22) Filed: Dec. 13, 2013

(65) Prior Publication Data

US 2014/0100549 A1 Apr. 10, 2014

Related U.S. Application Data

(63) Continuation of application No. 12/523,311, filed as application No. PCT/IB2007/000958 on Apr. 13, 2007, now Pat. No. 8,641,656.

(30) Foreign Application Priority Data

Jan. 17, 2007 (FR) ..................................... 07 00298

(51) Int. Cl.
*A61M 1/00* (2006.01)
*A61M 1/36* (2006.01)
*G06F 19/00* (2011.01)

(52) U.S. Cl.
CPC .......... *A61M 1/3656* (2014.02); *G06F 19/3431* (2013.01); *G06F 19/3481* (2013.01); *A61M 1/3653* (2013.01)

(58) Field of Classification Search
CPC .............. A61M 1/3653; A61M 1/3656; G06F 19/3481; G06F 19/3431
USPC .................... 604/4.01–6.16; 706/54; 709/203
See application file for complete search history.

(56) References Cited

U.S. PATENT DOCUMENTS

| 5,321,550 A | 6/1994 | Maruyama et al. |
| 5,453,576 A | 9/1995 | Krivitski |

(Continued)

FOREIGN PATENT DOCUMENTS

| EP | 0 547 025 A1 | 6/1993 |
| EP | 0 920 877 A1 | 6/1999 |
| EP | 0 928 614 A1 | 7/1999 |
| WO | 00/24440 A1 | 5/2000 |
| WO | 03/066135 A1 | 8/2003 |
| WO | 2006/031186 A1 | 3/2006 |

OTHER PUBLICATIONS

Gotch Frank A. and Sargent John A., "A mechanistic analysis of the National Cooperative Dialysis Study (NCDS)", Kidney International, vol. 28 (1985), pp. 526-534.
National Kidney Foundation KDOQI, "Clinical Practice Guidelines for Vascular Access—Guideline 4. Detection of Access Dysfunction: Monitoring, Surveillance, and Diagnostic Testing", 2006, pp. 1-25.
National Kidney Foundation KDOQI, "Clinical Practice Guidelines for Vascular Access—Guideline 5. Treatment of Fistula Complications", 2006, pp. 1-10.

*Primary Examiner* — Philip R Wiest
(74) *Attorney, Agent, or Firm* — K&L Gates LLP

(57) ABSTRACT

The invention relates to a calculation and control system for the determination of the state of a vascular access of a patient intended to follow successive sessions of extracorporeal blood treatment by extraction and return of the blood via the vascular access, the system comprising: means for determining the value of at least one hemodynamic extracorporeal parameter of the patient for at least two sessions; means for determining the value of the purification effectiveness of the treatment for at least two sessions; programmed means for determining a risk score relating to the state of the vascular access of the patient as a function of at least two values of the hemodynamic extracorporeal parameter and of at least two determined values of the purification effectiveness.

43 Claims, 5 Drawing Sheets

(56) References Cited

U.S. PATENT DOCUMENTS

| | | |
|---|---|---|
| 5,510,716 A | 4/1996 | Buffaloe, IV et al. |
| 5,510,717 A | 4/1996 | Buffaloe, IV et al. |
| 5,595,182 A | 1/1997 | Krivitski |
| 5,685,989 A | 11/1997 | Krivitski et al. |
| 6,110,384 A | 8/2000 | Goux et al. |
| 8,641,656 B2 * | 2/2014 | Bene .......................... 604/6.09 |
| 2004/0225201 A1 | 11/2004 | McNair |
| 2005/0020960 A1 | 1/2005 | Brugger et al. |
| 2005/0228241 A1 | 10/2005 | McNair |

\* cited by examiner

FOLLOW-UP OF THE VASCULAR ACCESS OF A DIALYZED PATIENT

TECHNICAL FIELD OF THE INVENTION

The present invention relates to the monitoring of the vascular access of a patient subjected to successive sessions of extracorporeal blood treatment, and more particularly relates to an innovative and improved procedure and innovative and improved devices for determining the state of the vascular access of the patient subjected to successive sessions of extracorporeal blood treatment.

STATE OF THE PRIOR ART

Extracorporeal blood treatment is used with patients incapable of effectively eliminating materials from their blood, for example in the case of a patient who suffers from a temporary or permanent failure of the kidneys. These patients and other patients can follow an extracorporeal treatment of the blood to add or eliminate materials in their blood, to maintain an acid-base equilibrium or to eliminate excessive body fluids, for example.

Extracorporeal treatment of the blood is typically performed by bleeding off the blood of the patient in a continuous stream, introducing the blood into a primary chamber of a treatment unit (or filter) in which the blood passes across a semi-permeable membrane.

The circuit comprising a needle for bleeding off the blood via the vascular access of the patient, a bleed-off line or arterial line, the first compartment of the treatment unit, a return line or venous line and a needle for returning the blood by injecting it via the vascular access, is called an extracorporeal blood circuit.

The semi-permeable membrane allows, in a selective manner, undesirable materials contained in the blood to pass across the membrane, from the primary chamber to the secondary chamber, and also allows, in a selective manner, beneficial materials contained in the liquid entering the secondary chamber to pass across the membrane to the blood entering the primary chamber, as a function of the type of treatment.

There are several types of extracorporeal blood treatments. Such treatments comprise, for example, hemodialysis, hemofiltration, hemodiafiltration, plasmapheresis, blood oxygenation, etc.

A patient may suffer from a permanent failure of the kidneys. In this case, he will have to undergo regular sessions, for example three times a week, of extracorporeal blood treatment with a relatively high blood extraction flowrate, namely roughly between 150 and 500 mL/min. The approximate duration of these sessions is from three to four hours.

At each hemodialysis session, one or two needles must be inserted into the vascular access of the patient. Normally the blood is bled off from a blood access and returned to the access. In hemodialysis or similar treatments, the blood access or the vascular access is created by surgical intervention, on the forearm for example, by an arterio-venous shunt, often called a fistula, for example an arterio-venous fistula of Cimino Brescia type. Thus the needle linked to the arterial line is introduced at an upstream position of the fistula while the needle linked to the venous line is introduced at a downstream position of the fistula. This makes it possible to obtain a blood access with a high blood flowrate, usable for at least several years. Alternatively to a fistula, it is possible to resort to an arterio-venous graft, performed by a transfer (cells, tissue or organ) from one point to another of one and the same patient or from one patient to another. For example the arterio-venous graft can be a connection generated from the radial artery at the wrist to the basilic vein.

The blood flowrate in the vascular access can rise to 800 mL/min or more, allowing extracorporeal delivery at the desired flowrate.

This vascular access, in spite of the careful introduction by the nurse of the needle or of the catheter for example, may suffer as a result of its repeated insertions and may lose its effectiveness. The vascular access may deteriorate over a relatively extended duration (after a few tens of sessions) or over a very short duration (in two sessions for example).

This can occur without the doctor or the nurse realizing sufficiently early.

In general, the doctor or the nurse may note a state of risk by noting a large measured increase in an extracorporeal hemodynamic parameter of the patient such as the arterial pressure, the venous pressure or the blood flowrate (flowrate via the arterial line for example). Nevertheless these variations may be due to several other reasons than the deterioration of the vascular access (needle poorly introduced, etc.).

There also exist methods of evaluation by instantaneous measurement of the flowrate in a vascular access such as a fistula.

Methods for measuring the flowrate of the vascular access and for monitoring recirculation (=the undesired circulation of already dialyzed blood in the arterial line) have previously been described.

They can use the injection of a marker into the blood to detect recirculation. These procedures normally include the measurement of a property in the extracorporeal blood circuit, and are described in particular in U.S. Pat. No. 5,685,989; U.S. Pat. No. 5,595,182; U.S. Pat. No. 5,453,576; U.S. Pat. No. 5,510,716; U.S. Pat. No. 5,510,717; U.S. Pat. No. 5,312,550, etc. Their drawback is the use of a marker introduced into the blood.

They can also use noninvasive techniques for measurements of the flowrate in the vascular access employing the Doppler effect or magnetic resonance imaging (MRI) for example.

Another method is also described in application WO03/066135 incorporated here by way of reference. For the record, the application relates to a procedure for determining the flowrate in a vascular access having an upstream position and a downstream position using a blood treatment apparatus including a blood treatment unit having a semi-permeable membrane delimiting a first chamber through which the blood removed from the vascular access passes and a second chamber through which the dialysis liquid passes, an arterial line and a venous line, connected respectively to an input and an output of the first chamber. The procedure includes a step of inversion of the two arterial and venous lines and comprises the measurement of the concentration or the conductivity downstream of the dialyzer before and after the inversion of the two lines. It will be understood that this method requires an additional intervention (inversion of the lines) and is necessarily implemented during the treatment, it is instantaneous, and very dependent on the conditions at the moment (blood pressure of the patient, etc.): the result thus has a changeable reliability.

Other methods of this type have been proposed in applications EP 0 928 614 and WO00/24440 with the measurement of the urea downstream of the dialyzer before and after inversion of the arterial and venous lines. They present the drawback of a special item of equipment for the measurement of the urea.

There does not exist, to the knowledge of the applicant, any system today making it possible to determine effectively and rapidly the state of the vascular access of the patient subjected to sessions of extracorporeal blood treatment of the risk levels of this state.

It is therefore necessary to offset this lack by a method and an apparatus for effectively determining the state of the vascular access of the patient, this allowing enhanced surveillance of the vascular access and faster attention further downstream to the drawbacks related to a failed vascular access.

ACCOUNT OF THE INVENTION

The invention relates to a calculation and control system (or control processing unit CPU) for the determination of the state of a vascular access of a patient intended to follow successive sessions (i,j) of extracorporeal blood treatment by extraction and return of the blood via the vascular access, the system comprising the following means:
  a) means for determining the value (P1i, P1j, P2i, P2j, . . . ) of at least one hemodynamic extracorporeal parameter (P1, P2 . . . ) of the patient for at least two sessions (i,j),
  b) means for determining the value (Ei, Ej) of the purification effectiveness of the treatment for at least two sessions (i,j),
  c) programmed means for determining a risk score relating to the state of the vascular access of the patient as a function of said at least two values (Pi, Pj) of the hemodynamic extracorporeal parameter and of said at least two determined values (Ei, Ej) of the purification effectiveness.

The invention also relates to a system for determining reliability of risk score of the state of a vascular access comprising means as follows:
  the system according to the invention,
  means for storing:
    I. a first risk score (S) determined over a first time interval defined between an anterior session and a posterior session and comprising more than two sessions,
    II. at least one second risk score (S') determined over at least one second time interval situated inside the first determined interval,
  programmed means for calculating the reliability as a function of the first score determined and at least of the second score determined (S, S').

The invention also relates to a computer comprising:
  storage means storing at least values of at least one extracorporeal hemodynamic parameter (P1i, . . . , P1j, . . . P2i, . . . , P2j . . . ) and purification effectiveness values (E(i), . . . , E(j)) relating to at least one patient subjected to several sessions (i, . . . j) of extracorporeal blood treatment,
  a calculation and control system according to the invention for the determination of the vascular state of the patient the parameter values of at least one of whose extracorporeal hemodynamic parameters (P1i, . . . , P1j, . . . P2i, . . . , P2j . . . ) and whose purification effectiveness values (E(i), . . . , E(j)) are stored in said storage means.

The invention also relates to an extracorporeal blood treatment machine comprising at least:
  a blood treatment unit capable of implementing an extracorporeal blood treatment by blood circulation via an extracorporeal blood circuit comprising an arterial line, a first chamber of a filter separated by a semi-permeable membrane, a venous line and by dialysate circulation in a second chamber of the filter,
  storage means storing at least values of at least one extracorporeal hemodynamic parameter and purification effectiveness values relating to at least one patient subjected to several sessions of extracorporeal blood treatment,
  a calculation and control system according to the invention for the determination of the vascular state of the patient the parameter values of at least one of whose extracorporeal hemodynamic parameters (P1i, . . . , P1j, . . . P2i, . . . , P2j . . . ) and whose purification effectiveness values (E(i), . . . , E(j)) are stored in said storage means.

The invention further relates to a network comprising:
  a server,
  at least one blood treatment machine linked to the server, each machine comprising:
    means for measuring and/or for calculating medical data relating to at least one extracorporeal hemodynamic parameter (P1i, . . . , P1j, . . . P2i, . . . , P2j . . . ) and to the purification effectiveness of the treatment (E(i), . . . , E(j)),
    means for sending at least part of these measured and/or calculated data to the server,
  the server comprising:
    means for receiving at least part of the medical data relating to extracorporeal blood treatments,
    storage means for storing the data received by the reception means from one or more blood treatment machines,
    a calculation and control system according to the invention, intended to operate on the basis of said received data,
  at least one station capable of communicating with the server for receiving at least the results of the implementation of said calculation and control system.

The invention also relates to a method of determining the state of a vascular access of a patient intended to follow successive sessions (i,j) of extracorporeal blood treatment by extraction and return of the blood via the vascular access, the method of determination comprising the following steps:
  a) determining the value (Pi, Pj) of at least one hemodynamic extracorporeal parameter (P) of the patient for at least two sessions (i,j),
  b) determining the value (Ei, Ej) of the purification effectiveness of the treatment for at least two sessions (i,j),
  c) determining a risk score relating to the state of the vascular access of the patient as a function of said at least two values (Pi, Pj) of the hemodynamic extracorporeal parameter and of said at least two determined values (Ei, Ej) of the purification effectiveness.

Finally, the invention relates finally to a computer program for determining the state of a vascular access of a patient, which program is loadable into the internal memory of a computer, comprising portions of computer program code for, when the program is executed by the computer, implementing the method according to the invention.

BRIEF DESCRIPTION OF THE DRAWINGS

We shall refer to the appended drawings in FIG. 1, 1', 2, 3, 4, and 5 in which.

DETAILED ACCOUNT OF THE INVENTION

Figure 1:
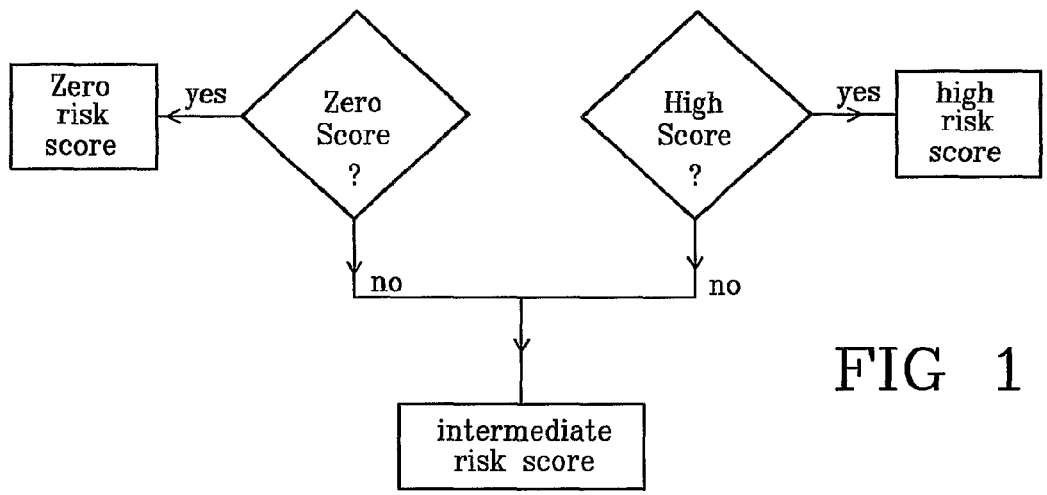
FIG. 1 represents the principal steps of the method of determining the risk score according to the invention, FIG. 1' represents an alternative of the order of the principal steps of the method of determining the risk score.
Figure 1:
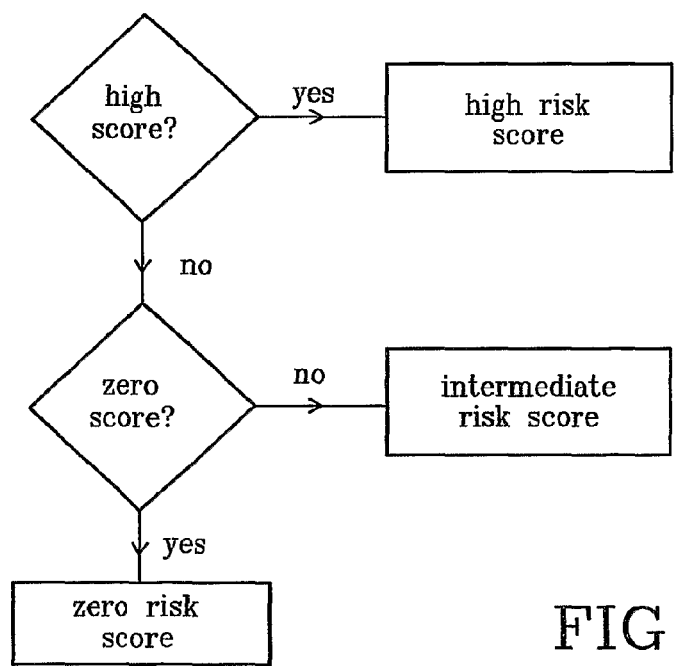

The invention relates to a calculation and control system for the determination of the state of a vascular access of a patient intended to follow successive sessions (i,j) of extracorporeal blood treatment by extraction and return of the blood via the vascular access, the system comprising the following means:
a) means for determining the value (P1i, P1j, P2i, P2j, ... ) of at least one hemodynamic extracorporeal parameter (P1, P2 ... ) of the patient for at least two sessions (i,j),
b) means for determining the value (Ei, Ej) of the purification effectiveness of the treatment for at least two sessions (i,j),
c) programmed means for determining a risk score relating to the state of the vascular access of the patient as a function of said at least two values (Pi, Pj) of the hemodynamic extracorporeal parameter and of said at least two determined values (Ei, Ej) of the purification effectiveness.

For the whole invention, the calculation and control system can take the form of a duly programmed analog, duly programmed digital calculation and control unit, comprising at least one microprocessor and at least one duly programmed memory. The memories may be one from among or a combination of the following memories: magnetic memory, RAM memory, ROM memory, or any other memory envisageable by the person skilled in the art.

The means for determining the value of at least one hemodynamic extracorporeal parameter and the means for determining the value of the purification effectiveness can be composed of:
at least one memory containing the value of these parameters and that the programmed means will be able to consult to ascertain the chosen values, and/or
apparatuses for detecting the corresponding parameters: pressure detectors or sensors, means for measuring the conductivity or the concentration of a substance in the blood, means for measuring the dialysance, the dialysis dose, the clearance,
a calculation and control unit which will be duly programmed to implement the method according to the invention.

The risk score can take three values:
S0) zero risk score (0) for a patient the state of whose vascular access is normal,
s1) intermediate risk score (1) for a patient the state of whose vascular access is doubtful,
s2) high risk score (2) for a patient the state of whose vascular access is alarming.

Thus the classification of the risk score of the vascular access can take three different values and gives an appreciation of the patients to be treated immediately by the doctor, of the cases with no problem for which the sessions ought to be conducted without modification until the next determination, and of the doubtful or uncertain cases to be monitored or for which it is necessary to go more deeply into the study of the curves measured during the last sessions. The doctor, following several tens of patients at the same time, will therefore be able to be steered, on reading the results of the system, very rapidly towards a patient requiring a check or an intervention on his vascular access.

Principal Decision Chart:

The system according to the invention has the programmed means for determining the risk score comprising programmed means for determining whether the risk score is high.

The system according to the invention has the programmed means for determining the risk score comprising programmed means for determining whether the risk score is zero.

The system according to the invention has the programmed means for determining the risk score comprising programmed means for, in the case where the risk score is determined neither high nor zero, considering the risk score to be intermediate.

The system according to the invention comprises the programmed means for determining the risk score which are programmed for determining whether the risk score is high before determining whether the risk score is zero.

As represented in the chart of FIGS. 1 and 1', the invention can comprise:
the determination of the risk score comprises the step of determining whether the risk score is high,
the determination of the risk score comprises the additional step of determining whether the risk score is zero,
the following additional step: if the risk score is determined neither high nor zero, then it is considered intermediate.

According to a first alternative proposed in the chart of FIG. 1, the steps of determination of the high or non-high score and determination of the zero or non-zero score can be implemented without temporal condition, simultaneously or otherwise.

According to a second alternative proposed in the chart of FIG. 1', the step of determining whether the risk score is zero is performed after the step of determining whether the risk score is high.

Parameters Involved:

In the system according to the invention, the hemodynamic extracorporeal parameter or parameters (P) have been measured for a session of extracorporeal blood treatment which consists in circulating the blood of the patient at an extracorporeal blood flowrate and in an extracorporeal blood circuit, this circuit comprising an arterial line where there exists an arterial pressure, a filter and a venous line where there exists a venous pressure. These hemodynamic extracorporeal parameters are chosen from among the group comprising:
Extracorporeal venous pressure (Pv),
Extracorporeal arterial pressure (Pa),
extracorporeal blood flowrate of the patient (Qb),
a parameter proportional to one of the three aforesaid parameters.

The hemodynamic extracorporeal parameters according to the invention are defined as pertaining to the mechanics of the blood circulation of the extracorporeal cardiovascular system.

The pressures will be measured by pressure sensors positioned on the arterial line and the venous line, the blood flowrate may be considered to be the imposed flowrate of a pump (for example peristaltic) positioned on the arterial line, and/or may be measured by a flowmeter on this line.

These hemodynamic extracorporeal parameters can change on account of the initial vascular access of the patient: for example, the smaller the caliber of the fistula (or central vein, etc.), the more the pressure regime reacts as in front of a difficult vascular access.

These hemodynamic extracorporeal parameters can also changed from one session to another if the same treatment means are not used from one session to another. It is indeed recommended that the puncture and treatment conditions be standardized by using an identical hemodialyzer, the same access on the arm, the same fistula, the same needle or the same needle diameter, etc. so as to strengthen the reliability of the method. Indeed, the recirculation in the fistula can depend, inter alia, on the extracorporeal blood flowrate, on the position of the needle inserted into the fistula, on the degree of stenosis of the fistula, it is therefore necessary to perform sessions with practices that are as regular as possible.

In the system according to the invention, the purification effectiveness (E) may have been measured for at least one session of extracorporeal blood treatment which consists in circulating the blood of the patient at an extracorporeal blood flowrate and in an extracorporeal blood circuit, this circuit comprising an extracorporeal arterial line, a filter and an extracorporeal venous line, the purification effectiveness (E) being equal to or a function of at least one of the following parameters:

- the dialysance (D), or
- the clearance (C), or
- the concentration of a substance contained in the blood before the filter (Cbin), or
- the concentration of a substance contained in the blood after the filter (Cbout) in the extracorporeal circuit, or
- the dialysis dose (KT/v) under conditions of equal session durations, or
- a parameter proportional to one of the five aforesaid parameters.

For the person skilled in the art, any physical or chemical parameter giving an indication as to the effectiveness of the transfer across the membrane will be taken into account.

It is necessary to specify that the purification effectiveness is not necessarily calculated during the extracorporeal blood treatment nor during the implementation of the method according to the invention.

An embodiment can have this effectiveness which, once calculated, will be stored in appropriate means. There will thereafter be, after the treatment session for example, during the implementation of the method according to the invention, access to the stored values.

An alternate mode can be the calculation of the effectiveness during treatment, this calculated effectiveness being used immediately for the method according to the invention.

It will be understood that the implementation of the method according to the invention is very separate from the extracorporeal blood treatment.

All this is also valid for the extracorporeal hemodynamic parameters.

Dialysance and the Clearance:

The dialysance (D) of a solute is defined as the mass of solute extracted from the blood per unit time divided by the difference between the concentration of this solute in the blood and of this solute in the dialysis liquid, on entry to the dialyzer or filter. This definition in general applies when the solute is present in the blood and in the fresh dialysis liquid (before entering the filter and contact with the blood via the semi-permeable membrane), or when the solute is present in the blood only. We shall for example speak in the first case of dialysance of sodium, of calcium or for example in the second case of dialysance of urea or of beta-2 microglobulin. The clearance of a solute is a particular case of the dialysance of a solute. It is the dialysance when the solute is present in the blood only and consequently is absent from the fresh dialysis liquid: we shall speak of urea clearance.

The dialysance or clearance of a solute can be calculated in different ways: on line in the extracorporeal circuit during the treatment or after the treatment, in-vivo during the treatment or after the treatment, once or several times by periodic samples, etc.

Patent EP 0547025, incorporated here by way reference, explains one mode of calculating the dialysance among others. For the record, it involves a procedure for determining a concentration of a substance in the blood of a patient undergoing a dialysis treatment in an artificial kidney (or filter or dialyzer) and/or the actual dialysance for said substance of the artificial kidney, the artificial kidney comprising an extracorporeal blood circuit connected to a dialyzer having a semipermeable membrane which delimits a first compartment for the flow of the blood and a second compartment for the flow of a dialysis liquid on the other face of the membrane, characterized by the steps of:

- circulating successively in the second compartment of the dialyzer, a first and a second liquid only differing by the concentration of the substance,
- measuring, in the first and second dialysis liquids, the conductivity or the concentration of the substance upstream and downstream of the dialyzer, and
- calculating, on the basis of the conductivity (by a conductimeter) or of the measured concentration of the substance in the first and second dialysis liquids, the concentration of the substance in the blood on entry to the dialyzer and/or the actual dialysance of the artificial kidney.

Dialysis Dose:

The total dialysis dose delivered is the integral of the values of average clearance or dialysance measured over a determined time interval.

The dialysis dose administered after a treatment time t can be regarded, according to the work of Sargent and Gotch, as the dimensionless ratio Kt/V, where K is the real clearance for the urea, t the elapsed treatment time, and V the volume of distribution of the urea, that is to say the total water volume of the patient (Gotch F A, Sargent S A. A mechanistic analysis of the National Cooperative Dialysis Study (NCDS). Kidney int 1985; 28: 526-34).

Patent EP0920877, incorporated here by way of reference, explains another mode of calculating a parameter representative of the effectiveness of the treatment, for example dialysance, clearance, dialysis dose or other parameter representative of the effectiveness of an extracorporeal blood treatment.

In the system according to the invention, the values of the hemodynamic extracorporeal parameter or parameters and of the purification effectiveness can be average values of these parameters over a treatment session.

These values can alternatively be an instantaneous value chosen at a moment t of the session, at the start, in the middle or at the end of the session, or can also be a median value, or any other mathematical value as exactly representative as possible of the parameter or of its evolution over a dialysis session.

Determination of the High Risk Score (2):

The system according to the invention has the programmed means for determining a high score comprising at least one from among the following means:

- programmed means for determining a first high score criterion,
- programmed means for determining a second high score criterion,
- programmed means for determining a third high score criterion,
- programmed means for determining a fourth high score criterion, programmed means for determining a fifth high score criterion,
and where the programmed means for determining whether the score is high are capable of sending as result:
a high score when at least one from among five criteria of high risk score is satisfied,
a non-high score when all the five criteria of high risk score are not satisfied.

For the whole invention, the means can be software codes which can take the form of source codes or of codes directly executable on a processor. The means for determining at least one from among the several criteria of high (or zero) score can be subroutines of the score determination means.

Specifically, if a single one among the 5 high score criteria is fulfilled, this suffices to deduce therefrom the high risk score.

It will also be possible to envisage a level of high risk score as a function of the number of high score criteria fulfilled. The more a patient has high score criteria fulfilled, the more the attention to this patient will take priority. The priority of the high risk score may also be calculated and employed for the presentation of the results to the doctor.

Figure 2:
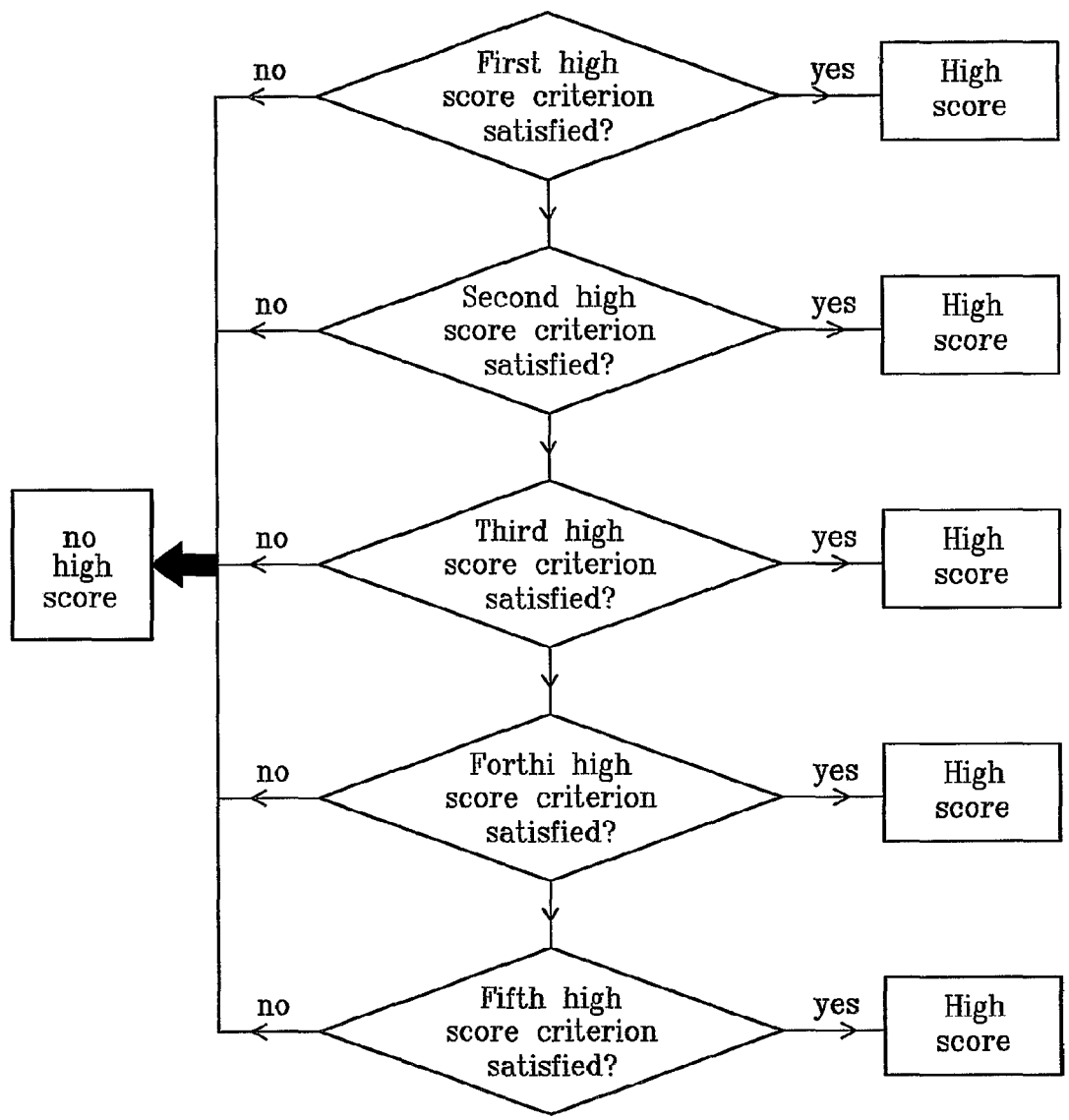
FIG. 2 represents the steps of the determination of the high or non-high risk score according to the invention.
Figure 3:
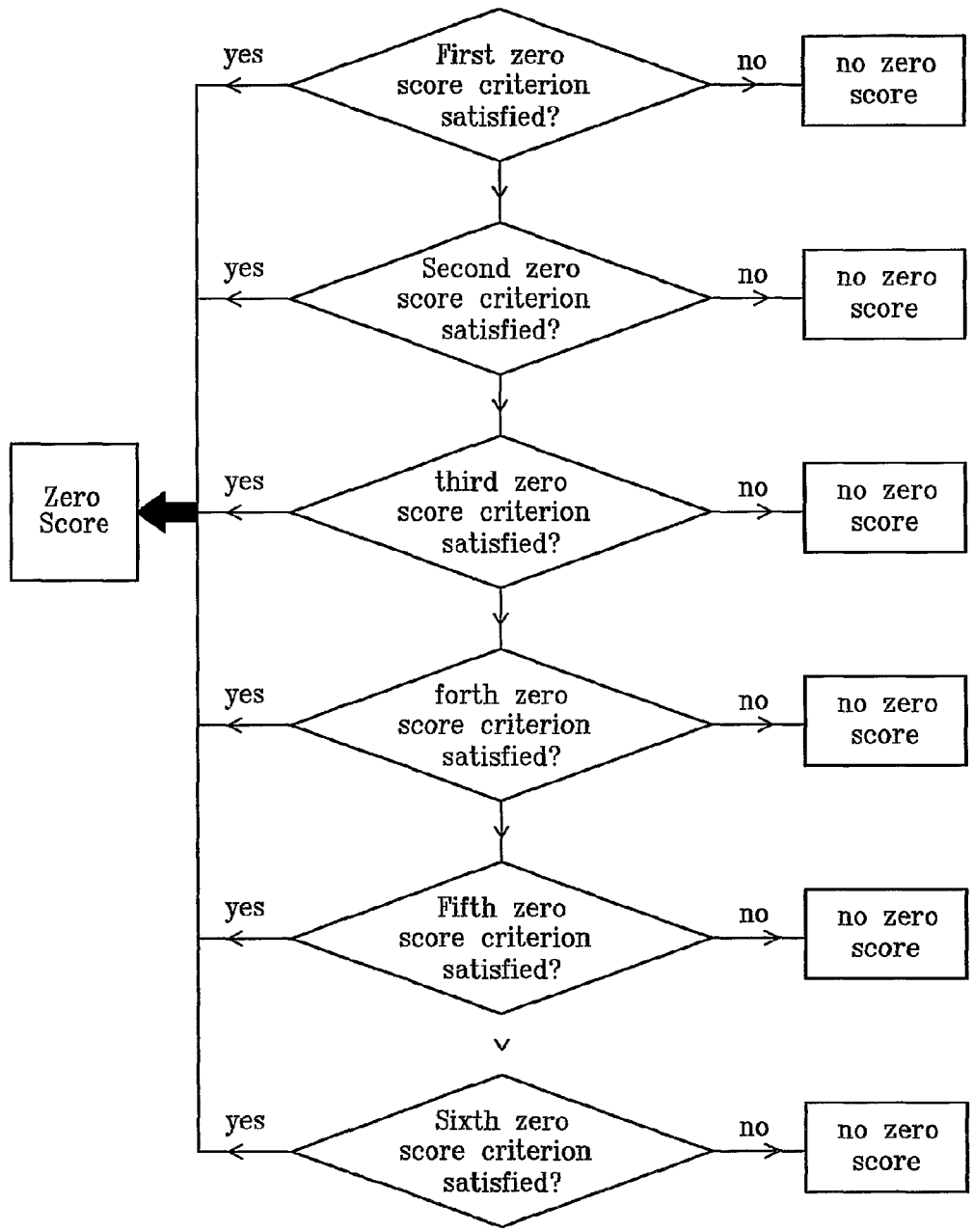
FIG. 3 represents the steps of the determination of the zero or non-zero risk score according to the invention.

Score Criteria:

It should be noted generally that, despite the step by step schematization of the chart of FIGS. 2 and 3, the satisfaction of the five high score criteria and of the six zero score criteria can be performed simultaneously and without imposition as regards the temporal order in which they are satisfied. The graphical representation is done only for the sake of clarity.

We shall examine in detail each of the five criteria of high risk score.

First Criterion of High Risk Score (2):

This involves determining whether a first criterion of high risk score is or is not satisfied.

According to the invention, the system has the programmed means for determining a first criterion of high risk score which are intended to operate at least as a function of the effectiveness parameters (P1i, P1j, P2i, P2j, ...) and of the extracorporeal blood flowrate (Qbi, ..., Qbj) determined for at least two sessions.

More particularly, the programmed means for determining the first criterion of high risk score can be intended at least to compare, for at least two sessions, each value of the effectiveness parameter (Ei, ..., Ej) of a session with a linear function of the value of the extracorporeal blood flowrate (Qbi, ..., Qbj) of the same session.

More particularly, the programmed means for determining the first satisfied high risk criterion can be intended to determine for at least two sessions whether each value of the determined effectiveness (E(i)) of a session lies on or below the straight line with equation:

$$E(i)=0.4*Qb(i)+40,$$

with Qb(i) the blood flowrate of the patient for the same session (i);
the score being high if this criterion is satisfied.

Specifically, the equation of this straight line corresponds to the following exemplary values:
For Qsg=250 mL/min, the effectiveness ought to be equal to or greater than 140.
For Qsg=300 mL/min, the effectiveness ought to be equal to or greater than 160.
For Qsg=350 mL/min, the effectiveness ought to be equal to or greater than 180.
For: Qsg=400 mL/min, the effectiveness ought to be equal to or greater than 200.

Generally throughout the present application, it should be noted that it involves values calculated for the given straight line equations, but that these compared data correspond to numerical values, since the units are not complied with.

Second Criterion of High Risk Score:

This involves determining whether a second high score criterion is or is not satisfied.

According to the invention, the system has the programmed means for determining a second criterion of high risk score which can be intended to operate at least as a function of the values of the venous pressure (Pvi, ..., Pvj) and of the arterial pressure (Pai, ..., Paj) determined for at least two sessions.

More particularly, the programmed means for determining the second criterion of high risk score can be intended to compare, for at least two sessions, the arterial pressure value and respectively the venous pressure value of a session with a predetermined arterial pressure value and respectively a predetermined venous pressure value.

More particularly, the system has the programmed means for determining the second criterion of high risk score that can be intended to determine for at least two sessions (i, j) whether:
the value of the venous pressure (Pv(i), ..., Pv(j)) is greater than or equal to 250 mmHg, and
the value of the arterial pressure (Pa(i), ..., Pa(j)) is less than −200 mmHg,
the score being high if both these conditions are satisfied.

The threshold values can of course vary in an interval about the values indicated, as a function of the patient, for example. A threshold value of venous pressure may lie between 200 and 300, about 250 preferably.

The more the number of sessions for which this first criterion examined is satisfied, the surer the result obtained for this criterion.

Third Criterion of High Risk Score:

This involves determining whether a third high score criterion is or is not satisfied.

According to the invention, the system has the programmed means for determining a third criterion of high risk score which can be intended to operate at least as a function of the evolution of the values of venous pressure (Pv(j)-Pv(i)), of the evolution of the values of arterial pressure (Pa(j)-Pa(i)) and of the evolution of the effectiveness values (E(j)-E(i)) determined between an anterior session (i) and a posterior session (j).

More particularly, the system has the programmed means for determining the third criterion of high risk score which can be intended to:
compare the evolution of the effectiveness (E(j)-E(i)) in relation to the value of the effectiveness of the anterior session (E(i)), and
compare the evolution of the arterial pressure (Pa(j)-Pa(i)) and venous pressure (Pv(j)-Pv(i)) with a predetermined value.

More particularly, the system has the programmed means for determining the third criterion of high risk score which can be intended to determine whether:
the absolute value of the variation in the effectiveness (E(j)-E(i)) between the anterior session (i) and the posterior session j) is greater than or equal to 10%, preferably 20%, of the value of the effectiveness of the anterior session (E(i)), and
the increase in the venous pressure (Pv(j)-Pv(i)) between the anterior session (i) and the posterior session (j) is greater than or equal to 50 mmHg, and the decrease in the arterial pressure (Pa(j)-Pa(i)) between the anterior session (i) and the posterior session (j) is less than or equal to 50 mmHg, the score being high if these three conditions are satisfied.

The threshold value of 50 mmHg is an indicative value, but the threshold can vary and be fixed onwards of 40 mmHg. This value can be chosen by the doctor as a function of the usual arterial or venous pressure of the patient. The same holds for the threshold percentage of the variation in the effectiveness.

Fourth Criterion of High Risk Score:

This involves determining whether a fourth high score criterion is or is not satisfied.

According to the invention, the system has the programmed means for determining a fourth criterion of high risk score which can be intended to operate at least as a function of the evolution of the values of venous pressure (Pv(j)-Pv(i)), of the evolution of the values of arterial pressure (Pa(j)-Pa(i)) and of the evolution of the effectiveness values (E(j)-E(i)) determined between an anterior session (i) and a posterior session (j).

More particularly, the system has the programmed means for determining the fourth criterion of high risk score which can be intended to compare each of said three parameter evolutions in relation to the value of the parameter of the anterior session.

More particularly, the system has the programmed means for determining the fourth criterion of high risk score which can be intended to determine whether:
the increase in the venous pressure (Pv(j)-Pv(i)) between the anterior session (i) and the posterior session (j) is greater than or equal to 10%, preferably 20% of the value of the venous pressure of the anterior session (Pv(i)), and
the decrease in the arterial pressure (Pa(j)-Pa(i)) between said sessions is greater than or equal to 10%, preferably 20% of the value of the arterial pressure (Pv(i)) of the anterior session,
the score being high if these two conditions are satisfied.

The threshold percentage value given is an indicative value, but the threshold can vary and be fixed between 10% and 20%. This value can be chosen by the doctor as a function of the usual arterial or venous pressure of the patient.

Fifth Criterion of High Risk Score:

This involves determining whether a fifth high score criterion is or is not satisfied.

The system according to the invention has the programmed means for determining the fifth criterion of high risk score which can be intended to operate at least as a function of the evolution of the purification effectiveness (E(i)-E(j)) between an anterior session (i) and a posterior session (j).

More particularly, the system has the programmed means for determining the fifth criterion of high risk score which can be intended to compare the evolution of the purification effectiveness (E(i)-E(j)) with a predetermined value.

More particularly, the system has the programmed means for determining the fifth criterion of high risk score which can be intended to determine whether the decrease in the purification effectiveness (E(i)-E(j)) between the anterior session (i) and the posterior session (j) is greater than or equal to 40 mL/min, the score being high if this condition is satisfied.

The threshold value of 40 mL/min is an indicative value, but the threshold can vary and be fixed onwards of 30 mL/min. This value can be chosen by the doctor as a function of the usual purification effectiveness in the patient.

Spacing of the Sessions Considered:

For the high score criteria, between an anterior session (i) and a posterior session (j), there may be, in terms of number of sessions, about ten or indeed several tens of sessions, or, in terms of weeks (at about 3 sessions per week), there may be between 2 weeks and 8 weeks, 3 weeks usually being chosen.

Generally, the high score criteria and the score criteria are determined as a function of the same group of sessions. This group of sessions may stretch between 2 weeks and 6 months, 3 weeks usually being chosen, or else this number of sessions may lie between about ten and several tens.

Generally, nevertheless, it will not be necessary to implement the method of determination according to the invention at each end of treatment session. The user will be able to find an effective monitoring compromise by implementing the method of the invention each three sessions (almost each week therefore) for example, or even each six sessions (almost each fortnight therefore).

Moreover, according to the invention:
for the determination of the first criterion of high risk score, if the number of sessions considered is greater than two, then the corresponding means of determination are intended to operate with each session considered;
for the determination of the second criterion of high risk score, if the number of sessions considered is greater than two, then the corresponding means of determination are intended to operate with at least two successive sessions (i,i+1);
for the determination of at least one from among the third, fourth and fifth criteria of high risk score, if the number of sessions considered is greater than two, then the corresponding means of determination are intended to operate by identifying the first temporal session considered as anterior session and by identifying the last temporal session considered as posterior session;
for the determination of at least one from among the third, fourth and fifth criteria of high risk score, if the number of sessions considered is greater than two, then the corresponding means of determination are intended to consider as temporal sessions those for which the values of at least one parameter considered are the most distant.

It may nevertheless also be valid to consider more than two sessions so as to discern the evolution with the passage of the sessions.

Determination of Zero Risk Score (0):

The system according to the invention comprises programmed means for determining the zero risk score comprising:
programmed means for determining a first zero score criterion,
programmed means for determining a second zero score criterion,
programmed means for determining a third zero score criterion,
programmed means for determining a fourth zero score criterion,
programmed means for determining a fifth zero score criterion,
programmed means for determining a sixth zero score criterion,
and where the programmed means for determining whether the score is zero are capable of sending as result:
a zero score when six criteria of zero risk score are all satisfied, or
a non-zero score when at least one from among the six zero score criteria is not satisfied.

First Criterion of Zero Risk Score:

This involves determining whether a first criterion of zero risk score is or is not satisfied.

According to the invention, the programmed means for determining a first criterion of zero risk score can be intended to operate at least as a function of the effectiveness parameter (E(i), ..., E(j)) and of the extracorporeal blood flowrate (Qb(i), ..., Qb(j)) determined for at least two sessions.

More particularly, the programmed means for determining the first criterion of zero risk score can be intended to compare, for at least two sessions, each value of the effectiveness parameter (E(i), ..., E(j)) of a session with a linear function of the value of the extracorporeal blood flowrate (Qb(i), ..., Qb(j)) of the same session.

More particularly, the programmed means for determining the first zero risk criterion can be intended to determine, for at least two sessions, whether each value of the determined effectiveness of a session lies on or above the straight line with equation:

$$E(i)=0.4*Qb(i)+40,$$

with Qb(i) the extracorporeal blood flowrate for the same session (i), the first criterion of zero risk score being satisfied in this case.

The more the number of sessions for which this first (or any other) criterion examined is satisfied, the surer the result obtained for this criterion.

Specifically, the equation of this straight line corresponds to the following exemplary values:
For Qb=250 mL/min, the effectiveness ought to be equal to or greater than 140.
For Qb=300 mL/min, the effectiveness ought to be equal to or greater than 160.
For Qb=350 mL/min, the effectiveness ought to be equal to or greater than 180.
For: Qb=400 mL/min, the effectiveness ought to be equal to or greater than 200.

Second Criterion of Zero Risk Score:

This involves determining whether a second criterion of zero risk score is or is not satisfied.

According to the invention, the system comprises programmed means for determining a second criterion of zero risk score which are intended to operate at least as a function of the values of the venous pressure (Pv(i), ..., Pv(j)) and of the arterial pressure (Pa(i), ..., Pa(j)) and of the values of the blood flowrate of the patient (Qb(i), ..., Qb(j)) determined for at least two sessions.

More particularly, the programmed means for determining a second criterion of zero risk score can be intended to compare, for at least two sessions, each value of the arterial pressure (Pa(i), ..., Pa(j)) with a linear function of the blood flowrate (Qb(i), ..., Qb(j)) of the session and each value of the venous pressure value (Pv(i), ..., Pv(j)) with a linear function of the blood flowrate of the session (Qb(i), ..., Qb(j)).

More particularly, the programmed means for determining the second criterion of zero risk score can be intended to determine for at least two sessions (i, ..., j):
whether each absolute value of the arterial pressure (Pa(i), ..., Pa(j)) determined per session is less than or equal to half the blood flowrate of the patient (Qb(i), ..., Qb(j)) for the session considered (i, ..., j), and
whether each value of the venous pressure (Pv(i), ..., Pv(j)) determined per session is less than or equal to half the blood flowrate of the patient (Qb(i), ..., Qb(j)) for the session considered (i, ..., j),
the second criterion of zero risk score being satisfied in this case.

Specifically, the equation of this straight line corresponds to the following exemplary values:
For Qb=250 mL/min, the venous pressure ought to be less than or equal to 125 mmHg and the arterial pressure ought to be greater than or equal to −125 mmHg
For Qb=300 mL/min, the venous pressure ought to be less than or equal to 150 mmHg and the arterial pressure ought to be greater than or equal to −150 mmHg
For Qb=350 mL/min, the venous pressure ought to be less than or equal to 175 mmHg and the arterial pressure ought to be greater than or equal to −175 mmHg
For Qb=400 mL/min, the venous pressure ought to be less than or equal to 200 mmHg and the arterial pressure ought to be greater than or equal to −200 mmHg).

Third Criterion of Zero Risk Score:

This involves determining whether a third criterion of zero risk score is or is not satisfied.

According to the invention, the system comprises programmed means for determining the third criterion of zero risk score which can be intended to operate at least as a function of the evolution of the extracorporeal blood flowrate (Qb(j)-Qb(i)) between an anterior session (i) and a posterior session (j).

More particularly, the programmed means for determining the third criterion of zero risk score can be intended to compare the evolution of the blood flowrate of the patient (Qb(j)-Qb(i)) with a predetermined value.

More particularly, the programmed means for determining the third criterion of zero risk score can be intended to determine whether the absolute value of the variation in the blood flowrate (|Qb(j)-Qb(i)|) between an anterior session (i) and a posterior session (j) is less than or equal to 20 mL/min, the third criterion of zero risk score being satisfied in this case.

The threshold difference value of 20 mL/min is an indicative value, but the threshold can vary and be fixed onwards of 10 mL/min. This value can be chosen by the doctor as a function of the usual blood flowrate of the patient during treatment, and would vary between 10 and 20, or indeed greater than 20.

Fourth Criterion of Zero Risk Score:

This involves determining whether a fourth criterion of zero risk score is or is not satisfied.

According to the invention, the system comprises programmed means for determining the fourth criterion of zero risk score which can be intended to operate at least as a function of the evolution of the values of arterial pressure (Pa(j)-Pa(i)) between an anterior session (i) and a posterior session (j).

More particularly, the programmed means for determining the fourth criterion of zero risk score can be intended to compare the evolution of the arterial pressure (Pa(j)-Pa(i)) with the value of the arterial pressure of the anterior session (Pa(i)).

More particularly, the programmed means for determining the fourth criterion of zero risk score can be intended to determine whether the variation in the arterial pressure (Pa(j)-Pa(i)) between the anterior session (i) and the posterior session (j) is less than or equal to 10%, preferably to 20%, of the arterial pressure (P(i)) of the anterior session, the fourth criterion of zero risk score being satisfied in this case.

The threshold percentage value given is an indicative value, but the threshold can vary and be fixed between 10% and 20%. This value can be chosen by the doctor as a function of the usual arterial pressure of the patient.

Fifth Criterion of Zero Risk Score:

This involves determining whether a fifth criterion of zero risk score is or is not satisfied.

According to the invention, the system comprises programmed means for determining the fifth criterion of zero risk score which can be intended to operate at least as a function of the evolution of the values of venous pressure ((Pv(j)-Pv(i))) between an anterior session and a posterior session.

More particularly, the programmed means for determining the fifth criterion of zero risk score can be intended to compare the evolution of the venous pressure ((Pv(j)-Pv(i))) with the value of the venous pressure of the anterior session (Pv (i)).

More particularly, the programmed means for determining the fifth criterion of zero risk score can be intended to determine whether the variation in the venous pressure ((Pv(j)-Pv (i)) between the anterior session (i) and the posterior session (j) is less than or equal to 10%, preferably to 20%, of the venous pressure (Pv(i)) of the anterior session, the fifth criterion of zero risk score being satisfied in this case.

The threshold percentage value given is an indicative value, but the threshold can vary and be fixed between 10% and 20%. This value can be chosen by the doctor as a function of the usual venous pressure of the patient.

Sixth Criterion of Zero Risk Score:

This involves determining whether a sixth criterion of zero risk score is or is not satisfied.

According to the invention, the system comprises programmed means for determining the sixth criterion of zero risk score which can be intended to operate at least as a function of the evolution of the effectiveness of the treatment ((E(j)-E(i)) between an anterior session (i) and a posterior session (j).

More particularly, the programmed means for determining the sixth criterion of zero risk score can be intended to compare the evolution of the effectiveness ((E(j)-E(i)) of the treatment with a predetermined value.

More particularly, the programmed means for determining a sixth criterion of zero risk score can be intended to determine whether the absolute value of the variation in the effectiveness of the treatment ((E(j)-E(i)) between the anterior session (i) and the posterior session (j) is less than or equal to 10 mL/min, the sixth criterion of zero risk score being satisfied in this case.

The threshold value of 10 mL/min is an indicative value, but the threshold can vary and be fixed onwards of 5 mL/min. This value can be chosen by the doctor as a function of the usual purification effectiveness in the patient.

In the system according to the invention:
for the determination of at least one from among the first and the second criteria of zero risk score, if the number of sessions considered is greater than two, then the corresponding means of determination are intended to operate with each session considered;
for the determination of at least one from among the third, fourth, fifth and sixth criteria of zero risk score, if the number of sessions considered is greater than two, then the corresponding means of determination are intended to operate by identifying the first temporal session considered as anterior session and by identifying the last temporal session considered as posterior session;
for the determination of at least one from among the third, fourth, fifth and sixth criteria of zero risk score, if the number of sessions considered is greater than two, then the corresponding means of determination are intended to consider as temporal sessions those for which the values of at least one parameter considered are the most distant.

In the system according to the invention, the treatment sessions considered are spread over at least two weeks, preferably over an interval lying between two weeks and six months, more preferably over an interval of three weeks.

System for Determining Reliability of Risk Score:

The invention pertains to a system for determining reliability of risk score of the state of a vascular access comprising means as follows:
the system for determining the state of a vascular access described above,
means for storing:
I. a first risk score (S) determined over a first time interval defined between an anterior session and a posterior session and comprising more than two sessions,
II. at least one second risk score (S') determined over at least one second time interval situated inside the first determined interval,
programmed means for calculating the reliability as a function of the first score determined and at least of the second score determined (S, S').

More particularly, when a number n of risk scores is determined by the system for determining the state of a vascular access, the programmed means for calculating the reliability can be intended to calculate the reliability percentage as equal or related to the ratio of the number of identities between the first risk score determined over the first interval and each of the other risk scores determined over an interval inside the first interval divided over the number n.

Particularly, the second time interval can have as posterior bound the posterior session of the first interval, or a bound temporally very close to the posterior bound the posterior session of the first interval.

It should be clearly noted that the system according to the invention is not necessarily implemented during the treatment. Preferably, it is implemented after a treatment session, if the parameters considered are mean parameters over a session.

The invention also relates to a computer comprising:
storage means storing at least values of at least one extracorporeal hemodynamic parameter (P1i, . . . , P1j, P2i, . . . P2j . . . ) and purification effectiveness values (E(i), . . . , E(j)) relating to at least one patient subjected to several sessions (i, . . . j) of extracorporeal blood treatment,
a calculation and control system according to the invention for the determination of the vascular state of the patient the parameter values of at least one of whose extracorporeal hemodynamic parameters (P1i, P1j, . . . P2i, . . . , P2j . . . ) and whose purification effectiveness values (E(i), . . . , E(j)) are stored in said storage means.

The invention also relates to an extracorporeal blood treatment machine comprising at least:
a blood treatment unit capable of implementing an extracorporeal blood treatment by blood circulation via an extracorporeal blood circuit comprising an arterial line, a first chamber of a filter separated by a semi-permeable membrane, a venous line and by dialysate circulation in a second chamber of the filter,
storage means storing at least values of at least one extracorporeal hemodynamic parameter and purification effectiveness values relating to at least one patient subjected to several sessions of extracorporeal blood treatment,
a calculation and control system according to the invention for the determination of the vascular state of the patient the parameter values of at least one of whose extracorporeal hemodynamic parameters (P1i, . . . , P1j, . . . P2i, . . . , P2j . . . ) and whose purification effectiveness values (E(i), . . . , E(j)) are stored in said storage means.

The invention also relates to a network comprising:
a server,
at least one blood treatment machine linked to the server, each machine comprising:
means for measuring and/or for calculating medical data relating to at least one extracorporeal hemodynamic parameter (P1i, ..., P1j, ... P2i, ..., P2j ...) and to the purification effectiveness of the treatment (E(i), ..., E(j)),
means for sending at least part of these measured and/or calculated data to the server,
the server comprising:
means for receiving at least part of the medical data relating to extracorporeal blood treatments,
storage means for storing the data received by the reception means from one or more blood treatment machines,
a calculation and control system according to the invention, intended to operate on the basis of said received data,
at least one station (client station for example) capable of communicating with the server for receiving at least the results of the implementation of said calculation and control system.

The station can comprise a unit for displaying the risk score results.

Figure 4:
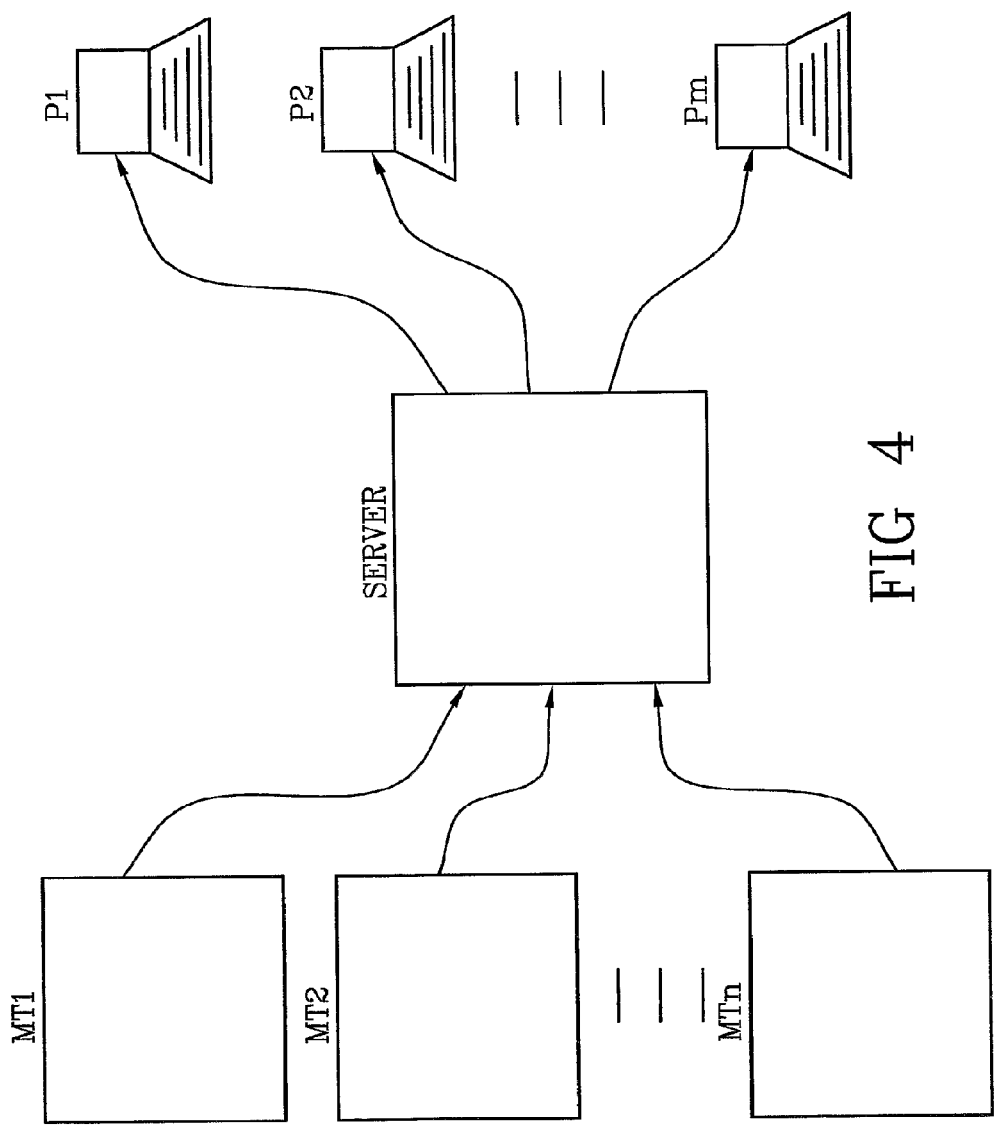
FIGS. 4 and 5 represent a diagram of a the complete software and hardware installation according to the invention.
Figure 5:
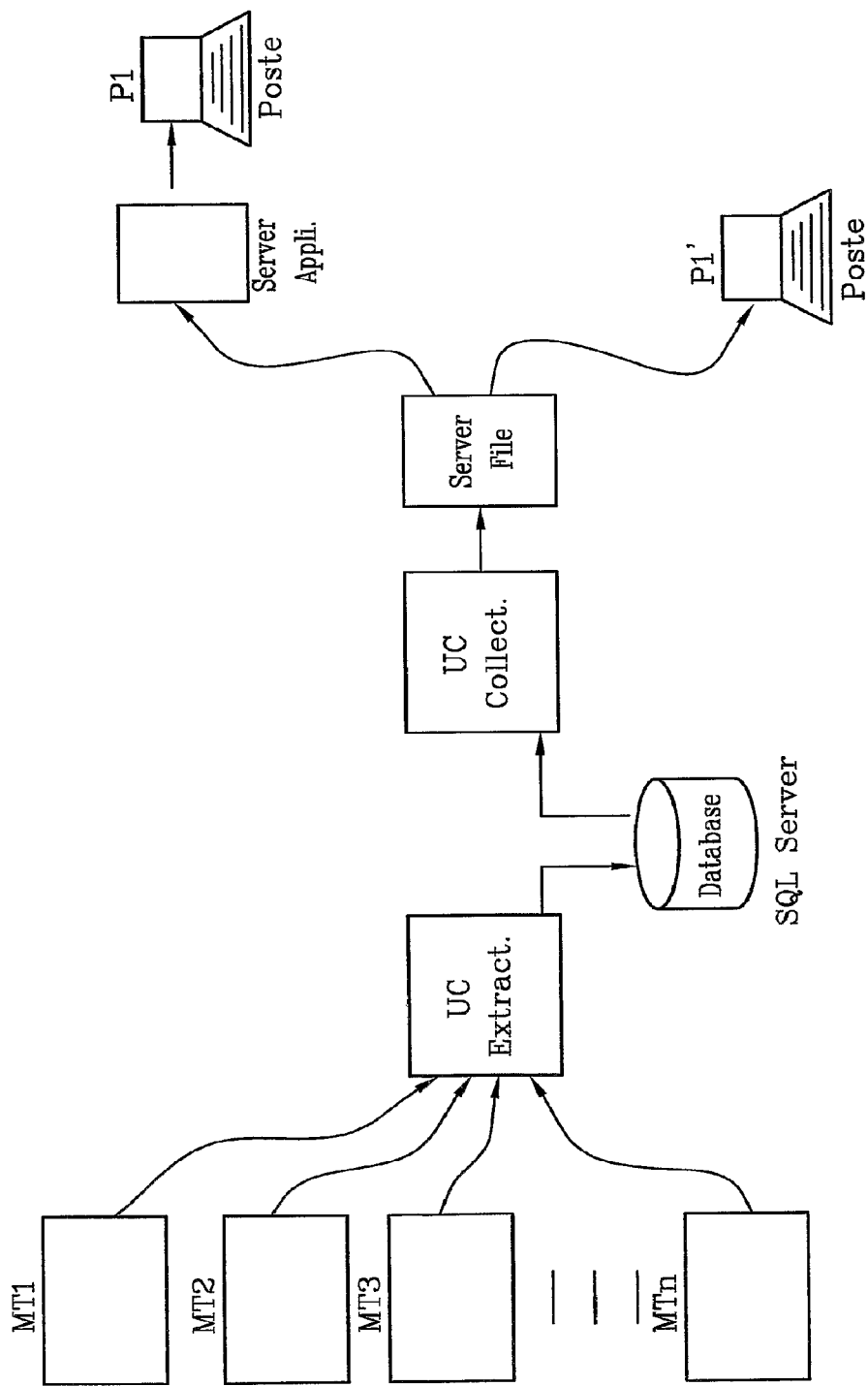

According to FIGS. 4 and 5, network examples are represented. These networks can comprise a part of elements in a treatment room, another part in the office of the doctor or else in another location where a coordinator works remotely for one or more clinics.

In FIG. 4 is shown diagrammatically a set of treatment machines MT1, Mt2, ... MTn which are placed in a clinic and which are each linked by a wire-based connection or by a wireless connection to a server.

This server is capable of receiving the data measured or calculated during and/or after the treatment sessions, is capable of storing all or some of the data produced by the treatment machine. When only part of the data is stored, it may have been extracted by a specific piece of software for collecting these data. This specific piece of collection software can be located in the treatment machine or in the server. This makes it possible to reduce the quantity of data to be stored which is very high due to the number of patients, of parameters and of sessions recorded. Such a system can for example take the form of that described in patent EP0428676 incorporated here by way of reference. For the record, this patent describes a surveillance method for monitoring a medical treatment performed by means of a dialysis machine linked to a central monitoring unit situated at a site distant from the site of the medical treatment, the method comprising the steps of:
measuring and/or formulating, on the site of the treatment, a plurality of parameters indicative of the operation of the dialysis machine;
selecting, from among the plurality of parameters, at least one particular parameter of interest,
applying, on the treatment site, at least one storage rule to the values taken by the selected parameter, so as to select from among these values a sub-group of values to be placed in memory,
placing in memory, on the treatment site, this sub-group of values at the central monitoring unit distant from the treatment site.
This method is described during the treatment, but can be implemented after the treatment and on a distant site for the selection step (as in FIG. 5).

Once the necessary parameters have been selected, the server implements the method according to the invention, this method being automated by the implementation of expert software.

The user will be able to access at least the results of the method according to the invention via a station linked to said server.

The links described can be made secure by known techniques for reasons of confidentiality of the data relating to a patient. Alternatively or additionally, the data can be, before sending, "anonymized" by the allocation of a code to each patient, without revealing the name of the patient during the data exchanges.

Also, the invention relates to a method of determining the state of a vascular access of a patient intended to follow successive sessions (i,j) of extracorporeal blood treatment by extraction and return of the blood via the vascular access, the method of determination comprising the following steps:
a) determining the value (Pi, Pj) of at least one hemodynamic extracorporeal parameter (P) of the patient for at least two sessions (i,j),
b) determining the value (Ei, Ej) of the purification effectiveness of the treatment for at least two sessions (i,j),
c) determining a risk score relating to the state of the vascular access of the patient as a function of said at least two values (Pi, Pj) of the hemodynamic extracorporeal parameter and of said at least two determined values (Ei, Ej) of the purification effectiveness.

This method preferably implemented automatically can be conducted in situ in the treatment room or remotely in a room of the clinic or of a data processing center.

In the method according to the invention, the risk score can take three values:
S0) zero risk score for a patient the state of whose vascular access is normal,
s1) intermediate risk score for a patient the state of whose vascular access is uncertain (or "doubtful"),
s2) high risk score for a patient the state of whose vascular access is alarming.

The determination of the risk score can comprise:
the step of determining whether the risk score is high,
the additional step of determining whether the risk score is zero,
the following additional step: if the risk score is determined neither alarming nor zero, then it is considered intermediate.

The step of determining whether the risk score is zero can be performed after the step of determining whether the risk score is high.

Parameters Involved:

In the method according to the invention, the hemodynamic extracorporeal parameter or parameters (P) have been measured for a session of extracorporeal blood treatment which consists in circulating the blood of the patient at an extracorporeal blood flowrate and in an extracorporeal blood circuit, this circuit comprising an arterial line where there exists an arterial pressure, a filter and a venous line where there exists a venous pressure.

These parameters can be chosen from among the group comprising:
Extracorporeal venous pressure (Pv),
Extracorporeal arterial pressure (Pa),
extracorporeal blood flowrate of the patient (Qb),
a parameter proportional to one of the three aforesaid parameters.

In the method according to the invention, the purification effectiveness (E) has been measured for a session of extracorporeal blood treatment which consists in circulating the blood of the patient at an extracorporeal blood flowrate and in an extracorporeal blood circuit, this circuit comprising an extracorporeal arterial line, a filter and an extracorporeal venous line, the purification effectiveness (E) being equal or a function of at least one of the following parameters:
- the dialysance (D), or
- the clearance (C), or
- the concentration of a substance contained in the blood before the filter (Cbin), or
- the concentration of a substance contained in the blood after the filter (Cbout) in the extracorporeal circuit, or
- the dialysis dose (KT/v), or
- a parameter proportional to one of the five aforesaid parameters.

The values of the hemodynamic parameter or parameters and of the purification effectiveness can of the average values of these parameters over a treatment session.

All the remarks made for the devices according to the invention are also valid for the method according to the invention.

Determination of the High Risk Score (2):

The method according to the invention comprises the step to determine if the score is high has:
- as result a high score when at least one from among five criteria of high risk score is satisfied,
- as result a non-high score when all the five criteria of high risk score are not satisfied.

Determination of the First Criterion of High Risk Score:

According to the invention, the determination of a first criterion of high risk score is at least a function of the effectiveness parameter and the extracorporeal blood flowrate determined for at least two sessions.

More particularly, the determination of the first criterion of high risk score is performed at least by comparing, for at least two sessions, each value of the effectiveness parameter of a session with a linear function of the value of the extracorporeal blood flowrate of the same session.

More particularly, the determination of the first satisfied high risk criterion consists in determining for at least two sessions whether each value of the determined effectiveness of a session lies on or below the straight line with equation:

$E(i)=0.4*Qb(i)+40$, with Qb(i) the blood flowrate of the patient for the same session (i); the score being high if this criterion is satisfied.

The more the number of sessions for which this first criterion examined is satisfied, the surer the result obtained for this criterion.

Second Criterion of High Risk Score:

According to the invention, the determination of a second criterion of high risk score is at least a function of the values of the venous pressure and the arterial pressure determined for at least two sessions.

More particularly, the determination of the second criterion of high risk score is made by comparing, for at least two sessions, the arterial pressure value and respectively the venous pressure value of a session with a predetermined arterial pressure value and respectively a predetermined venous pressure value. More particularly, the determination of the second criterion of satisfied high risk score consists in determining for at least two sessions (i, j) whether:
- the value of the venous pressure (Pv(i), Pv(j)) is greater than or equal to 250 mmHg, and
- the value of the arterial pressure (Pa(i), Pa(j)) is less than −200 mmHg for at least two sessions (i,j);
the score being high if these two conditions are satisfied.

Third Criterion of High Risk Score:

According to the invention, the determination of a third criterion of high risk score is at least a function of the evolution of the values of venous pressure, of the evolution of the values of arterial pressure and of the evolution of the effectiveness values determined between an anterior session (i) and a posterior session (D.

More particularly, the determination of the third criterion of high risk score comprises:
- the comparison of the evolution of the effectiveness (E(j)-E(i)) in relation to the value of the effectiveness of the anterior session (E(i)), and
- the comparison of the evolution of the arterial pressure (Pa(j)-Pa(i)) and venous pressure (Pv(j)-Pv(i)) with a predetermined value.

More particularly, the determination of the third criterion of high risk score consists in determining whether:
- the absolute value of the variation in the effectiveness (E(j)-E(i)) between the anterior session (i) and the posterior session (j) is greater than or equal to 10%, preferably 20% of the value of the effectiveness of the anterior session (E(i)), and
- the increase in the venous pressure (Pv(j)-Pv(i)) between the anterior session (i) and the posterior session (1) is greater than or equal to 50 mmHg, and
- the decrease in the arterial pressure (Pa(j)-Pa(i)) between the anterior session (i) and the posterior session CO is less than or equal to 50 mmHg, the score being high if these three conditions are satisfied.

Fourth Criterion of High Risk Score:

According to the invention, the determination of a fourth criterion of high risk score is at least a function of the evolution of the values of venous pressure (Pv(j)-Pv(i)), the evolution of the values of arterial pressure (Pa(j)-Pa(i)) and the evolution of the effectiveness values (E(j)-E(i)) determined between an anterior session (i) and a posterior session (j).

More particularly, the determination of the fourth criterion of high risk score comprises the comparison of each of said three parameter evolutions in relation to the value of the parameter of the anterior session.

More particularly, the determination of the fourth criterion of high risk score consists in determining whether:
- the increase in the venous pressure (Pv(j)-Pv(i)) between the anterior session (i) and the posterior session (j) is greater than or equal to 10%, preferably 20% of the value of the venous pressure of the anterior session (Pv(i)), and
- the decrease in the arterial pressure (Pa(j)-Pa(i)) between said sessions is greater than or equal to 10%, preferably 20% of the value of the arterial pressure (Pv(i)) of the anterior session,
the score being high if these two conditions are satisfied.

Fifth Criterion of High Risk Score:

According to the invention, the determination of a fifth criterion of high risk score is at least a function of the evolution of the purification effectiveness (E(i)-E(j)) between an anterior session (i) and a posterior session (j).

More particularly, the determination of the fifth criterion of high risk score comprises the comparison of the evolution of the purification effectiveness (E(i)-E(j)) with a predetermined value.

More particularly, the determination of the fifth criterion of satisfied high risk score consists in determining whether the decrease in the purification effectiveness (E(i)-E(j)) between the anterior session (i) and the posterior session (j) is greater than or equal to 40 mL/min, the score being high if this condition is satisfied.

According to the invention:
for the determination of the first criterion of high risk score, if the number of sessions considered is greater than two, then the determination can be made for each session considered.
for the determination of the second criterion of high risk score, if the number of sessions considered is greater than two, then the determination can be made for at least two successive sessions (i,i+1).
for the determination of at least one from among the third, fourth and fifth criteria of high risk score, if the number of sessions considered is greater than two, then the anterior session can be the first temporal session considered and the posterior session can be the last temporal session considered,
for the determination of at least one from among the third, fourth and fifth criteria of high risk score, if the number of sessions considered is greater than two, then the temporal sessions considered can be those for which the values of at least one parameter considered are the most distant.

Determination of Zero Risk Score (0):
This determination has as result:
a zero score when six criteria of zero risk score are all fulfilled, or
a non-zero score when at least one from among the six zero score criteria is not fulfilled.

First Criterion of Zero Risk Score:
According to the invention, the determination of a first criterion of zero risk score is at least a function of the effectiveness parameter and the extracorporeal blood flowrate determined for at least two sessions.

More particularly, the determination of the first criterion of zero risk score is performed by comparing, for at least two sessions, each value of the effectiveness parameter of a session with a linear function of the value of the extracorporeal blood flowrate of the same session.

More particularly, the determination of the first zero risk criterion consists in determining, for at least two sessions, if each value of the determined effectiveness of a session lies on or above the straight line with equation:

$$E(i)=0.4*Qb(i)+40,$$

with Qb(i) the extracorporeal blood flowrate for the same session (i), the first criterion of zero risk score being satisfied in this case.

Second Criterion of Zero Risk Score:
According to the invention, the determination of a second criterion of zero risk score is at least a function of the values of the venous pressure and the arterial pressure and the values of the blood flowrate of the patient determined for at least two sessions.

More particularly, the determination of the second criterion of zero risk score is made by comparing, for at least two sessions, each value of the arterial pressure (Pa(i), . . . , Pa(j)) with a linear function of the blood flowrate (Qb(i), . . . , Qb(j)) of the session and each value of the venous pressure value (Pv(i), . . . , Pv(j)) with a linear function of the blood flowrate of the session (Qb(i), . . . , Qb(j)).

More particularly, the determination of the second criterion of zero risk score consists in determining for at least two sessions (i, j):
whether each absolute value of the arterial pressure (Pa(i), Pa(j)) determined per session is less than or equal to half the blood flowrate of the patient (Qb(i), . . . , Qb(j)) for the session considered (i,j), and
whether each value of the venous pressure (Pv(i), . . . , Pv(j)) determined per session is less than or equal to half the blood flowrate of the patient (Qb(i), . . . , Qb(j)) for the session considered (i,j),
the second risk score criterion being considered zero in this case.

Third Criterion of Zero Risk Score:
According to the invention, the determination of a third criterion of zero risk score is at least a function of the evolution of the extracorporeal blood flowrate (Qb(j)-Qb(i)) between an anterior session (i) and a posterior session (j).

More particularly, the determination of the third criterion of zero risk score comprises the comparison of the evolution of the blood flowrate of the patient with a predetermined value.

More particularly, the determination of the third criterion of zero risk score consists in determining whether the absolute value of the variation in the blood flowrate (|Qb(j)-Qb(i)|) between an anterior session (i) and a posterior session (j) is less than or equal to 20 mL/min, the third risk score criterion being considered zero in this case.

Fourth Criterion of Zero Risk Score:
According to the invention, the determination of a fourth criterion of zero risk score is at least a function of the evolution of the values of arterial pressure (Pa(j)-Pa(i)) between an anterior session (i) and a posterior session (j).

More particularly, the determination of the fourth criterion of zero risk score comprises the comparison of the evolution of the arterial pressure (Pa(j)-Pa(i)) with the value of the arterial pressure (Pa(i)) of the anterior session (i).

More particularly, the determination of the fourth criterion of zero risk score consists in determining whether the variation in the arterial pressure (Pa(j)-Pa(i)) between the anterior session (i) and the posterior session (j) is less than or equal to 10%, preferably to 20%, of the arterial pressure (Pa(i)) of the anterior session, the fourth risk score criterion being considered zero in this case.

Fifth Criterion of Zero Risk Score:
According to the invention, the determination of a fifth criterion of zero risk score is at least a function of the evolution of the values of venous pressure (Pv(j)-Pv(i)) between an anterior session (i) and a posterior session (j).

More particularly, the determination of the fifth criterion of zero risk score comprises the comparison of the evolution of the venous pressure (Pv(j)-Pv(i)) with the value of the venous pressure of the anterior session (Pv(i)).

More particularly, the determination of the fifth criterion of zero risk score consists in determining whether the variation in the venous pressure (Pv(j)-Pv(i)) between the anterior session (i) and the posterior session (j) is less than or equal to 10%, preferably to 20%, of the venous pressure (Pv(i)) of the anterior session, the fifth risk score criterion being considered zero in this case.

Sixth Criterion of Zero Risk Score:
According to the invention, the determination of a sixth criterion of zero risk score is at least a function of the evolution of the effectiveness of the treatment ((E(j)-E(i)) between an anterior session (i) and a posterior session (j).

More particularly, the determination of the sixth criterion of zero risk score comprises the comparison of the evolution of the effectiveness of the treatment ((E(j)-E(i)) with a predetermined value.

More particularly, the determination of the sixth criterion of zero risk score consists in determining whether the absolute value of the variation in the effectiveness of the treatment ((E(j)-E(i)) between the anterior session (i) and the posterior session (j) is less than or equal to 10 mL/min, the sixth risk score criterion being considered zero in this case.

In the method of determining the zero risk score:
for the determination of at least one from among the first and the second criteria of zero risk score, if the number of sessions considered is greater than two, then the determination is made for each session considered,
for the determination of at least one from among the third, fourth, fifth and sixth criteria of zero risk score, if the number of sessions considered is greater than two, then the anterior session can be the first temporal session considered and the posterior session can be the last temporal session considered,
for the determination of at least one from among the third, fourth, fifth and sixth criteria of zero risk score, if the number of sessions considered is greater than two, then the temporal sessions considered can be those for which the values of at least one parameter considered are the most distant.

In the method according to the invention, the treatment sessions considered are spread over at least two weeks, preferably over an interval lying between 2 weeks and 6 months, more preferably over an interval of 3 weeks.

The invention also relates to a method of determining reliability of risk score of the state of a vascular access comprising the following steps:
first implementation of the method of determining the state of a vascular access over a first time interval defined between an anterior session and a posterior session and comprising more than two sessions,
taking into account of the first risk score determined,
at least one second implementation of the method of determining the state of a vascular access over at least one second time interval situated inside the first determined interval,
taking into account of the second risk score determined,
calculating the reliability as a function of the first score determined and at least of the second score determined.

More particularly, when a number n of risk scores is determined by n implementations of the method of determining the state of a vascular access, the calculation of a reliability percentage is operated by the ratio of the number of identities between the first risk score determined over the first interval and each of the other risk scores determined over an interval inside the first interval divided over the number n.

More particularly, the second time interval has as posterior bound the posterior session of the first interval.

It should be clearly noted that the method according to the invention is not necessarily implemented during the treatment. Preferably, it is implemented after a treatment session, if the parameters considered are mean parameters over a session.

The invention relates finally to a computer program for determining the state of a vascular access of a patient, which program is loadable into the internal memory of a computer, comprising portions of computer program code for, when the program is executed by the computer, implementing the method of determining the state of the vascular access and/or the method of determining reliability of risk score of the state determined.

This program can be recorded on a readable medium in a computer, the medium being an optical and/or magnetic data memory or a volatile memory medium.

Concerning the invention in general, the risk score takes 3 values according to the information provided by the parameters examined.

The zero risk score corresponds to the patients examined who are stable in a normality zone for a recent and sufficiently long time period.

The intermediate risk score corresponds to the patients examined who may be outside of the normality zone, but who do not have any recent aggravation of their vascular access making it possible to envisage a short-term complication.

The high risk score corresponds to the patients examined exposed to a short-term complication which threatens the functionality of the vascular access.

ADVANTAGES OF THE INVENTION

The invention affords a maximum of advantages of which the main ones are listed here:
swiftness of the evaluation of a risk of the vascular access,
implementation of the invention without necessary additional hardware;
time saving of additional treatment or intervention on the patient;
saving of additional labor costs, of consumable medical apparatus, of hardware (use of Doppler . . . )
implementation of the invention without additional manipulation during treatment, and without intervention during dialysis sessions, therefore without producing disturbances,
alert levels sorted by priority with a high risk score and an intermediate risk score;
remote monitoring of several patients and/or in one or more clinics,
remote monitoring by a doctor of a home dialysis patient,
anticipation of the at risk state of the vascular access before the start of a dialysis session,
ranking according to several levels of significance of the risk of the vascular access,
the doctor can be sent the calculated scores directly.

In patients with zero score, the invention makes it possible to avoid expensive explorations and/or examinations repeated by regular (each week for example) and systematic analysis, In patients with intermediate score, a rather more normal situation is detected, but the analysis steers the doctor towards complementary examinations and/or steers the doctor to prescribe an update of the prescription for the extracorporeal treatment, In patients with high score, there is a time gain in the indication of invasive exploration, and therefore there are better chances of saving a vascular access and of accessing possibilities of efficacious treatments in regard to extrarenal purification.

The invention claimed is:
1. A method of determination of the state of a vascular access of a patient intended to follow successive sessions (i,j) of extracorporeal blood treatment by extraction and return of the blood via the vascular access, each successive extracorporeal blood treatment session comprising circulating the blood of the patient, at an extracorporeal blood flow rate, in an extracorporeal blood circuit having an extracorporeal arterial line, a filter and an extracorporeal venous line, the method comprising the following steps:
a) determining a value (P1i, P1j, P2i, P2j, . . . ) of at least one hemodynamic extracorporeal parameter (P1, P2 . . . ) of the patient for at least two sessions (i,j),
b) determining a value (Ei, Ej) of purification effectiveness of the extracorporeal blood treatment for at least two sessions (i,j), wherein the purification effectiveness is equal or a function of at least one in the group of:
the dialysance (D),
the clearance (C),
the concentration of a substance contained in the blood before the filter (Cbin),
the concentration of a substance contained in the blood after the filter (Cbout) in the extracorporeal circuit,
the dialysis dose (KT/v) under conditions of equal session durations,
c) determining a risk score relating to the state of the vascular access of the patient as a function of at least two values (Pi, Pj) of the hemodynamic extracorporeal parameter and of at least two determined values (Ei, Ej) of the purification effectiveness.

2. The method of claim 1, wherein the risk score takes one of the following three values:
(s0) zero risk score (0) for a patient the state of whose vascular access is normal,
(s1) intermediate risk score (1) for a patient the state of whose vascular access is doubtful,
(s2) high risk score (2) for a patient the state of whose vascular access is alarming.

3. The method of claim 2, wherein determining the risk score comprises determining whether the risk score is high.

4. The method of claim 2, wherein determining the risk score comprises determining whether the risk score is zero.

5. The method of claim 2, wherein determining the risk score comprises—where the risk score is determined neither high nor zero—considering the risk score to be intermediate.

6. The method of claim 2, wherein determining the risk score comprises determining whether the risk score is high before determining whether the risk score is zero.

7. The method of claim 1, wherein the hemodynamic extracorporeal parameter or parameters (P) having been measured for a session of extracorporeal blood treatment which consists in circulating the blood of the patient at an extracorporeal blood flowrate and in an extracorporeal blood circuit, this circuit comprising an arterial line where there exists an arterial pressure, a filter and a venous line where there exists a venous pressure, these hemodynamic extracorporeal parameters are chosen from among the group comprising:
extracorporeal venous pressure (Pv),
extracorporeal arterial pressure (Pa),
extracorporeal blood flow rate of the patient (Qb),
a parameter proportional to one of the three aforesaid parameters.

8. The method of claim 1, wherein the values of the hemodynamic extracorporeal parameter or parameters and of the purification effectiveness are average values of these parameters over a treatment session.

9. A method of determination of the state of a vascular access of a patient intended to follow successive sessions (i,j) of extracorporeal blood treatment by extraction and return of the blood via the vascular access, the method comprising the following steps:
a) determining a value (P1i, P1j, P2i, P2j, . . . ) of at least one hemodynamic extracorporeal parameter (P1, P2 . . . ) of the patient for at least two sessions (i,j),
b) determining a value (Ei, Ej) of purification effectiveness of the extracorporeal blood treatment for at least two sessions (i,j),
c) determining a risk score relating to the state of the vascular access of the patient as a function of at least two values (Pi, Pj) of the hemodynamic extracorporeal parameter and of at least two determined values (Ei, Ej) of the purification effectiveness, wherein determining the risk score comprises determining whether the risk score is high and wherein determining whether the risk score is high comprises at least the following:
determining a first criterion of high risk score,
determining a second criterion of high risk score,
determining a third criterion of high risk score,
determining a fourth criterion of high risk score,
determining a fifth criterion of high risk score,
and wherein determining whether the risk score is high causes as result:
a high score when at least one from among five criteria of high risk score is satisfied,
a non-high score when all the five criteria of high risk score are not satisfied.

10. The method of claim 9, wherein determining a first criterion of high risk score is a function of the values of the effectiveness parameters (P1i, P1j, P2i, P2j, . . . ) and the extracorporeal blood flow rate (Qbi, . . . , Qbj) for at least two sessions.

11. The method of claim 10, wherein determining the first criterion of high risk score comprises comparing, for at least two sessions, each value of the effectiveness parameter (Ei, . . . , Ej) of a session with a linear function of the value of the extracorporeal blood flow rate (Qbi, . . . , Qbj) of the same session.

12. The method of claim 10, wherein determining if the first criterion of high risk score is satisfied comprises determining for at least two sessions whether each value of the determined effectiveness (E(i)) of a session lies on or below the straight line with equation:

$$E(i)=0{,}4*Qb(i)+40,$$

with Qb(i) the blood flowrate of the patient for the same session (i);
the score being high if this criterion is satisfied.

13. The method of claim 9, wherein determining a second criterion of high risk score is a function of the values of the venous pressure (Pvi, . . . , Pvj) and of the arterial pressure (Pai, . . . , Paj) determined for at least two sessions.

14. The method of claim 13, wherein determining the second criterion of high risk score comprises comparing, for at least two sessions, the arterial pressure value and respectively the venous pressure value of a session with a predetermined arterial pressure value and respectively a predetermined venous pressure value.

15. The method of claim 13, wherein determining the second criterion of high risk score comprises determining for at least two sessions (i, j) whether:
the value of the venous pressure (Pv(i), . . . , Pv(j)) is greater than or equal to 250 mmHg,
and
the value of the arterial pressure (Pa(i), . . . , Pa(j)) is less than −200 mmHg,
the score being high if these two conditions are satisfied.

16. The method of claim 9, wherein determining a third criterion of high risk score is function of the evolution of the values of venous pressure (Pv(j)-Pv(i)), of the evolution of the values of arterial pressure (Pa(j)-Pa(i)) and of the evolution of the effectiveness values (E(j)-E(i)) determined between an anterior session (i) and a posterior session (j).

17. The method of claim 16, wherein determining the third criterion of high risk comprises to:
compare the evolution of the effectiveness (E(j)-E(i)) in relation to the value of the effectiveness of the anterior session (E(i)), and compare the evolution of the arterial pressure (Pa(j)-Pa(i)) and venous pressure (Pv(j)-Pv(i)) with a predetermined value.

18. The method of claim 16, wherein determining the third criterion of high risk score comprises to determine whether:
the absolute value of the variation in the effectiveness (E(j)-E(i)) between the anterior session (i) and the posterior session (j) is greater than or equal to 10%, preferably 20%, of the value of the effectiveness of the anterior session (E(i)), and
the increase in the venous pressure (Pv(j)-Pv(i)) between the anterior session (i) and the posterior session (j) is greater than or equal to 50 mmHg, and
the decrease in the arterial pressure (Pa(j)-Pa(i)) between the anterior session (i) and the posterior session (j)) is less than or equal to 50 mmHg,
the score being high if these three conditions are satisfied.

19. The method of claim 9, wherein determining a fourth criterion of high risk score is a function of the evolution of the values of venous pressure (Pv(j)-Pv(i)), of the evolution of the values of arterial pressure (Pa(j)-Pa(i)) and of the evolution of the effectiveness values (E(j)-E(i)) determined between an anterior session (i) and a posterior session (j).

20. The method of claim 19, wherein determining the fourth criterion of high risk score comprises comparing each of said three parameter evolutions in relation to the value of the parameter of the anterior session.

21. The method of claim 19, wherein determining the fourth criterion of high risk score comprises determining whether:
the increase in the venous pressure (Pv(j)-Pv(i)) between the anterior session (i) and the posterior session (j) is greater than or equal to 10%, preferably 20% of the value of the venous pressure of the anterior session (Pv(i)), and
the decrease in the arterial pressure (Pa(j)-Pa(i)) between said sessions is greater than or equal to 10%, preferably 20% of the value of the arterial pressure (Pv(i)) of the anterior session,
the score being high if these two conditions are satisfied.

22. The method of claim 9, wherein determining the fifth criterion of high risk score is function of the evolution of the purification effectiveness (E(i)-E(j)) between an anterior session (i) and a posterior session (j).

23. The method of claim 22, wherein determining the fifth criterion of high risk score comprises comparing the evolution of the purification effectiveness (E(i)-E(j)) with a predetermined value.

24. The method of claim 22, wherein determining the fifth criterion of high risk score comprises determining whether the decrease in the purification effectiveness (E(i)-E(j)) between the anterior session (i) and the posterior session (j) is greater than or equal to 40 mL/min, the score being high if this condition is satisfied.

25. The method of claim 9, wherein for the determination of the first criterion of high risk score, if the number of sessions considered is greater than two, then the corresponding determination is function of each session considered.

26. The method of claim 9, wherein for the determination of the second criterion of high risk score, if the number of sessions considered is greater than two, then the corresponding determination is a function of at least two successive sessions (i,i+1).

27. The method of claim 9, wherein for the determination of at least one from among the third, fourth and fifth criteria of high risk score, if the number of sessions considered is greater than two, then the corresponding determination identifies the first temporal session considered as anterior session and the last temporal session considered as posterior session.

28. The method of claim 9, wherein for the determination of at least one from among the third, fourth and fifth criteria of high risk score, if the number of sessions considered is greater than two, then the corresponding determination identifies as temporal sessions those for which the values of at least one parameter considered are the most distant.

29. A method of determination of the state of a vascular access of a patient intended to follow successive sessions (i,j) of extracorporeal blood treatment by extraction and return of the blood via the vascular access, the method comprising the following steps:
a) determining a value (P1i, P1j, P2i, P2j, . . . ) of at least one hemodynamic extracorporeal parameter (P1, P2 . . . ) of the patient for at least two sessions (i,j),
b) determining a value (Ei, Ej) of purification effectiveness of the extracorporeal blood treatment for at least two sessions (i,j),
c) determining a risk score relating to the state of the vascular access of the patient as a function of at least two values (Pi, Pj) of the hemodynamic extracorporeal parameter and of at least two determined values (Ei, Ej) of the purification effectiveness, wherein determining the risk score comprises determining whether the risk score is zero and wherein determining whether the risk score is zero comprises at least the following:
determining a first criterion of zero risk score,
determining a second criterion of zero risk score,
determining a third criterion of zero risk score,
determining a fourth criterion of zero risk score,
determining a fifth criterion of zero risk score,
determining a sixth criterion of zero risk score,
and where determining whether the risk score is zero sends as result:
a zero score when six criteria of zero risk score are all satisfied, or
a non-zero score when at least one from among the six zero score criteria is not satisfied.

30. The method of claim 29, wherein determining a first criterion of zero risk score is a function of the effectiveness parameter (E(i), . . . , E(j)) and of the extracorporeal blood flow rate (Qb(i), . . . , Qb(j)) determined for at least two sessions, further wherein determining the first criterion of zero risk score comprises to compare, for at least two sessions, each value of the effectiveness parameter (E(i), . . . , E(j)) of a session with a linear function of the value of the extracorporeal blood flowrate (Qb(i), . . . , Qb(j)) of the same session.

31. The method of claim 29, wherein determining a first criterion of zero risk score is function of the effectiveness parameter (E(i), . . . , E(j)) and of the extracorporeal blood flow rate (Qb(i), . . . , Qb(j)) determined for at least two sessions, further wherein determining the first criterion of zero risk score comprises determining, for at least two sessions, whether each value of the determined effectiveness of a session lies on or above the straight line with equation:

$$E(i)=0.4*Qb(i)+40,$$

with Qb(i) the extracorporeal blood flowrate for the same session (i), the first criterion of zero risk score being satisfied in this case.

32. The method of claim 29, wherein determining a second criterion of zero risk is a function of the values of the venous pressure (Pv(i), . . . , Pv(j)) and of the arterial pressure (Pa(i), . . . , Pa(j)) and of the values of the blood flow rate of the patient (Qb(i), . . . , Qb(j)) determined for at least two sessions, further wherein determining the second criterion of zero risk score comprises comparing, for at least two sessions, each value of the arterial pressure (Pa(i), ..., Pa(j)) with a linear function of the blood flow rate (Qb(i), ..., Qb(j)) of the session and each value of the venous pressure value (Pv(i), ..., Pv(j)) with a linear function of the blood flow rate of the session (Qb(i), ..., Qb(j)).

33. The method of claim 29, wherein determining a second criterion of zero risk is a function of the values of the venous pressure (Pv(i), ..., Pv(j)) and of the arterial pressure (Pa(i), ..., Pa(j)) and of the values of the blood flow rate of the patient (Qb(i), ..., Qb(j)) determined for at least two sessions, further wherein determining the second criterion of zero risk score comprises determining for at least two sessions (i, j):
whether each absolute value of the arterial pressure (Pa(i), ..., Pa(j)) determined per session is less than or equal to half the blood flow rate of the patient (Qb(i), ..., Qb(j)) for the session considered (i, ... j), and
whether each value of the venous pressure (Pv(i), ..., Pv(j)) determined per session is less than or equal to half the blood flow rate of the patient (Qb(i), ..., Qb(j)) for the session considered (i, ..., j),
the second criterion of zero risk score being satisfied in this case.

34. The method of claim 29, wherein determining the third criterion of zero risk score is a function of the evolution of the extracorporeal blood flow rate (Qb(j))-Qb(i)) between an anterior session (i) and a posterior session (j), further wherein determining the third criterion of zero risk score comprises comparing the evolution of the blood flow rate of the patient (Qb(j)-Qb(i)) with a predetermined value.

35. The method of claim 29, wherein determining the third criterion of zero risk score is a function of the evolution of the extracorporeal blood flow rate (Qb(j)-Qb(i)) between an anterior session (i) and a posterior session (j), further wherein determining the third criterion of zero risk score comprises determining whether the absolute value of the variation in the blood flow rate (|Qb(j))-Qb(i)|) between an anterior session (i) and a posterior session (j) is less than or equal to 20 mL/min, the third criterion of zero risk score being satisfied in this case.

36. The method of claim 29, wherein determining the fourth criterion of zero risk score is a function of the evolution of the values of arterial pressure (Pa(j)-Pa(i)) between an anterior session (i) and a posterior session (j), further wherein determining the fourth criterion of zero risk score comprises comparing the evolution of the arterial pressure (Pa(j)-Pa(i)) with the value of the arterial pressure of the anterior session (Pa(i)).

37. The method of claim 29, wherein determining the fourth criterion of zero risk score is a function of the evolution of the values of arterial pressure (Pa(j)-Pa(i)) between an anterior session (i) and a posterior session (j), further wherein determining the fourth criterion of zero risk score comprises determining whether the variation in the arterial pressure (Pa(j)-Pa(i)) between the anterior session (i) and the posterior session (j) is less than or equal to 10%, preferably to 20%, of the arterial pressure (P(i)) of the anterior session, the fourth criterion of zero risk score being satisfied in this case.

38. The method of claim 29, wherein determining the fifth criterion of zero risk score is a function of the evolution of the values of venous pressure ((Pv(j))-Pv(i)) between an anterior session and a posterior session, further wherein determining the fifth criterion of zero risk score comprises comparing the evolution of the venous pressure ((Pv(j)-Pv(i)) with the value of the venous pressure of the anterior session (Pv(i)).

39. The method of claim 29, wherein determining the fifth criterion of zero risk score is a function of the evolution of the values of venous pressure ((Pv(j))-Pv(i)) between an anterior session and a posterior session, further wherein determining the fifth criterion of zero risk score comprises determining whether the variation in the venous pressure ((Pv(j))-Pv(i)) between the anterior session (i) and the posterior session (j) is less than or equal to 10%, preferably to 20%, of the venous pressure (Pv(i)) of the anterior session, the fifth criterion of zero risk score being satisfied in this case.

40. The method of claim 29, wherein determining the sixth criterion of zero risk score is a function of the evolution of the effectiveness of the treatment ((E(j))-E(i)) between an anterior session (i) and a posterior session (j), further wherein determining the sixth criterion of zero risk score comprises comparing the evolution of the effectiveness ((E(j))-E(i)) of the treatment with a predetermined value.

41. The method of claim 29, wherein determining the sixth criterion of zero risk score is a function of the evolution of the effectiveness of the treatment ((E(j))-E(i)) between an anterior session (i) and a posterior session (j), further wherein determining the sixth criterion of zero risk score comprises determining whether the absolute value of the variation in the effectiveness of the treatment ((E(j))-E(i)) between the anterior session (i) and the posterior session (j) is less than or equal to 10 mL/min, the sixth criterion of zero risk score being satisfied in this case.

42. A method of determining reliability of risk score of the state of a vascular access comprising a determination of the state of a vascular access of a patient intended to follow successive sessions (i,j) of extracorporeal blood treatment by extraction and return of the blood via the vascular access, the method comprising the following steps:
a) determining a value (P1i, P1j, P2i, P2j, ...) of at least one hemodynamic extracorporeal parameter (P1, P 2 ...) of the patient for at least two sessions (i,j),
b) determining a value (Ei, Ej) of purification effectiveness of the extracorporeal blood treatment for at least two sessions (i,j),
c) determining a risk score relating to the state of the vascular access of the patient as a function of at least two values (Pi, Pj) of the hemodynamic extracorporeal parameter and of at least two determined values (Ei, Ej) of the purification effectiveness, determining a risk score comprising determining:
I. a first risk score (S) determined over a first time interval defined between an anterior session and a posterior session and comprising more than two sessions,
II. at least one second risk score (S') determined over at least one second time interval situated inside the first determined interval, and
d) calculating the reliability as a function of the first score determined and at least of the second score determined (S, S').

43. The method of claim 42, wherein, when a number n of risk scores is determined, the calculating of the reliability comprises calculating the reliability percentage as equal or related to the ratio of the number of identities between the first risk score determined over the first interval and each of the other risk scores determined over an interval inside the first interval divided over the number n.

* * * * *